United States Patent
Lo et al.

(10) Patent No.: US 11,938,546 B2
(45) Date of Patent: Mar. 26, 2024

(54) PRECISION CONTROL OF LARGE-SCALE GREEN SYNTHESIS OF BIODEGRADABLE GOLD NANODANDELIONS AS POTENTIAL RADIOTHERANOSTICS

(71) Applicants: NATIONAL HEALTH RESEARCH INSTITUTES, Zhunan Town (TW); Leu-Wei Lo, Zhunan Town (TW)

(72) Inventors: Leu-Wei Lo, Zhunan Town (TW); Yao-Chen Chuang, Zhunan Town (TW)

(73) Assignee: NATIONAL HEALTH RESEARCH INSTITUTES, Zhunan Town (TW)

( * ) Notice: Subject to any disclaimer, the term of this patent is extended or adjusted under 35 U.S.C. 154(b) by 286 days.

(21) Appl. No.: 17/286,439

(22) PCT Filed: Oct. 18, 2018

(86) PCT No.: PCT/US2018/056540
§ 371 (c)(1),
(2) Date: Apr. 16, 2021

(87) PCT Pub. No.: WO2020/081088
PCT Pub. Date: Apr. 23, 2020

(65) Prior Publication Data
US 2021/0387258 A1    Dec. 16, 2021

(51) Int. Cl.
*B22F 9/24* (2006.01)
*A61K 9/14* (2006.01)
(Continued)

(52) U.S. Cl.
CPC ............ *B22F 9/24* (2013.01); *A61K 41/0038* (2013.01); *B22F 1/054* (2022.01);
(Continued)

(58) Field of Classification Search
None
See application file for complete search history.

(56) References Cited

U.S. PATENT DOCUMENTS

2012/0107242 A1*   5/2012   Wang ................. A61K 47/6923
                                                            424/9.1
2020/0017815 A1*   1/2020   Kawano ............... C12N 5/0068

FOREIGN PATENT DOCUMENTS

CN        105158456 A   * 12/2015
CN        105665736 A     6/2016
(Continued)

OTHER PUBLICATIONS

Suarasan, S. et al., "One-pot, green synthesis of gold nanoparticles by gelatin and investigation of their biological effects on Osteoblast cells", Colloids and Surfaces B: Biointerfaces, vol. 132, pp. 122-131, available online May 15, 2015.*
(Continued)

*Primary Examiner* — George Wyszomierski
(74) *Attorney, Agent, or Firm* — Muncy, Geissler, Olds & Lowe, P.C.

(57) ABSTRACT

The present invention relates to a new type of metabolizable flower-like gold nanodandelion (GND), which possesses features: (1) large scale green synthesis with high monodispersity and a circa 100% yield; (2) cellular/physiological degradability; (3) precision control of the shape, petal number and size; (4) highly efficient radiotheranostics encompassing better enhanced CT contrast and pronounced x-ray induced ROS generation than conventional spherical AuNP.

13 Claims, 16 Drawing Sheets

(51) Int. Cl.
  *A61K 41/00* (2020.01)
  *B22F 1/054* (2022.01)
  *B82Y 5/00* (2011.01)
  *B82Y 40/00* (2011.01)

(52) U.S. Cl.
  CPC ..... *B22F 2301/255* (2013.01); *B22F 2304/05* (2013.01); *B82Y 5/00* (2013.01); *B82Y 40/00* (2013.01)

(56) References Cited

FOREIGN PATENT DOCUMENTS

| CN | 104308175 B | | 4/2017 |
|---|---|---|---|
| JP | 2013233101 A | * | 11/2013 |
| JP | 2018083780 A | * | 5/2018 |

OTHER PUBLICATIONS

English translation of JP 2013233101 (originally published Nov. 21, 2013) obtained from PE2E search.*

English translation of CN 105158456 (originally published Dec. 16, 2015) obtained from PE2E search.*

English Translation of JP 2018083780 (originally published May 31, 2018), obtained from PE2E search.*

Misawa, Masaki "Generation of reactive oxygen species induced by gold nanoparticles under x-ray and UV Irradiations", Nanomedicine, Nanotechnology, Biology and Medicine, Jan. 18, 2011 Elsevier, NL, vol. 7, Issue No. 5, Jan. 18, 2011, pp. 604-614 (XP-0282975630).

Bastús; Neus G et al.; "Kinetically Controlled Seeded Growth Synthesis of Citrate-Stabilized Gold Nanoparticles of up to 200 nm: Size Focusing versus Ostwald Ripening", Langmuir, American Chemical Society, vol. 27, Issue No. 17, Jul. 5, 2011, pp. 11098-11105 (XP-055235288).

Wang, Yi-Cheng et al.; "Spectroscopic and microscopic investigation of gold nanoparticle nucleation and growth mechanisms using gelatin as a stabilizer", Journal of Nanoparticle Research ; An Interdisciplinary Forum for Nanoscale Science and Technology, Kluwer Academic Publishers, vol. 14, Issue No. 10, Sep. 25, 2012, pp. 1-11 (XP-035125674).

Shi, W et al.; "Synthesis and Characterization of Gold Nanoparticles with Plasmon AbsorbanceWavelength Tunable fromVisible to Near Infrared Region", International Scholarly Research Network. ISRN Nanomaterials, vol. 2012, Article ID 659043, Oct. 15, 2012, 9 pages (XP-055704293).

Hainfeld, James F et al.; "Gold nanoparticle imaging and radiotherapy of brain tumors in mice", Nanomedicine, Future Medicine Ltd., London, GB, vol. 8, Issue No. 10, Sep. 30, 2013, pp. 1601-1609 (XP-055232202).

Sivera, Martin et al.; "Silver Nanoparticles Modified by Gelatin with Extraordinary pH Stability and Long-Term Antibacterial Activity", PLOS ONE, vol. 9, Issue No. 8, Aug. 6, 2014, 6 pages (XP-055704301).

* cited by examiner

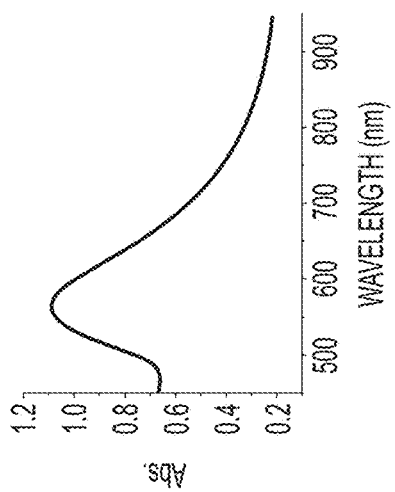
FIG. 2C
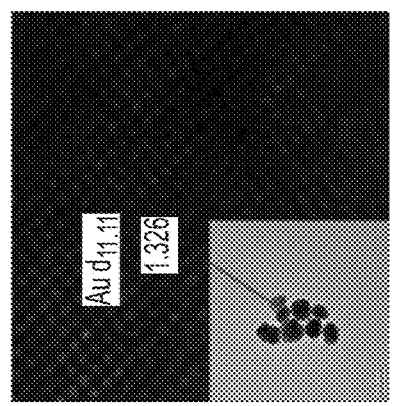
FIG. 2F
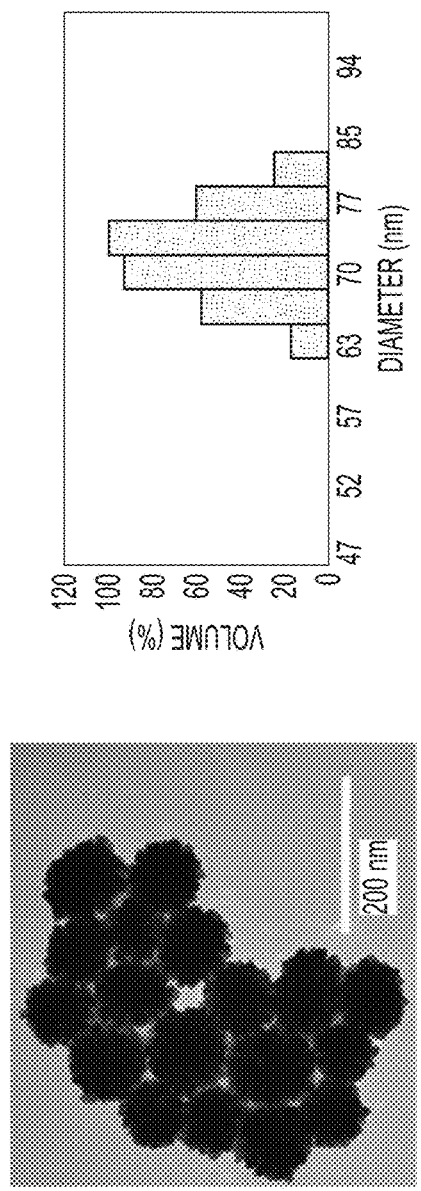
FIG. 2B
FIG. 2E
FIG. 2A
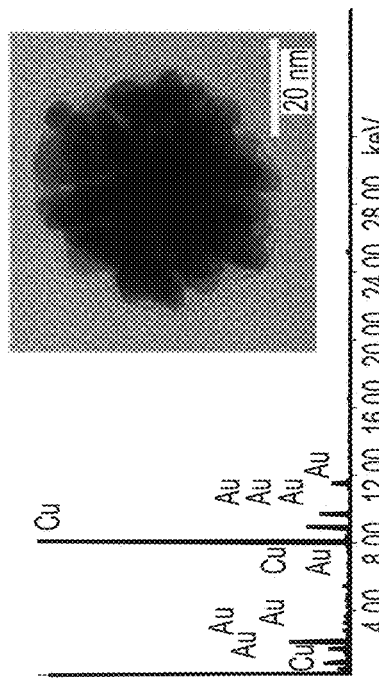
FIG. 2D

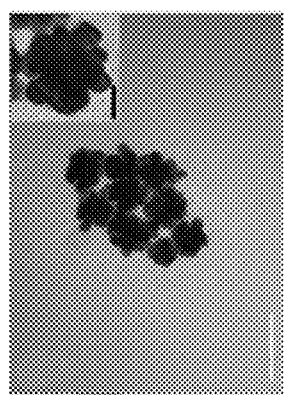
FIG. 4L
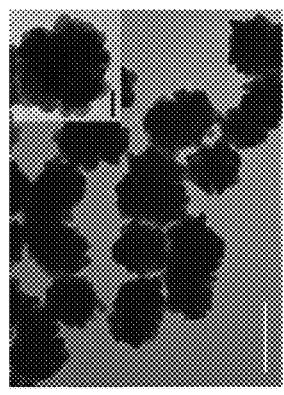
FIG. 4K
FIG. 4J
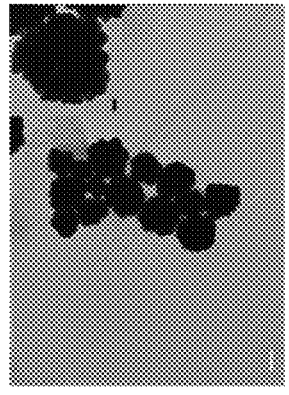
FIG. 4I

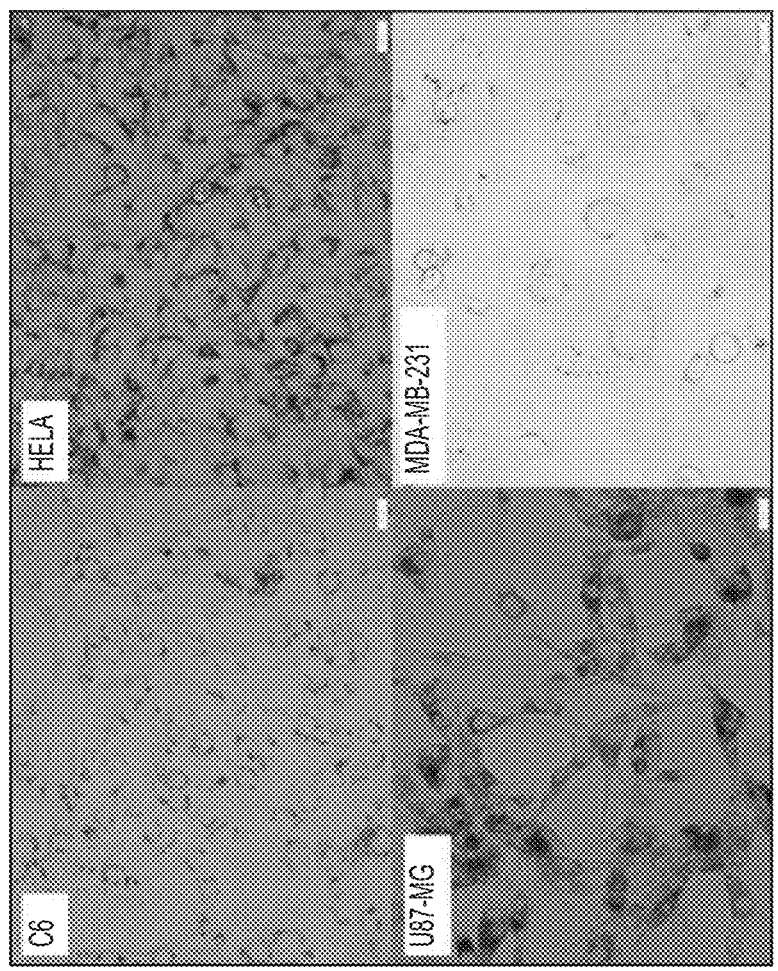
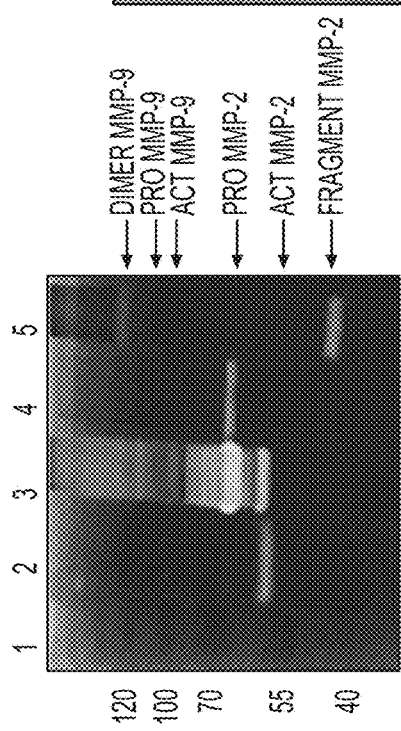
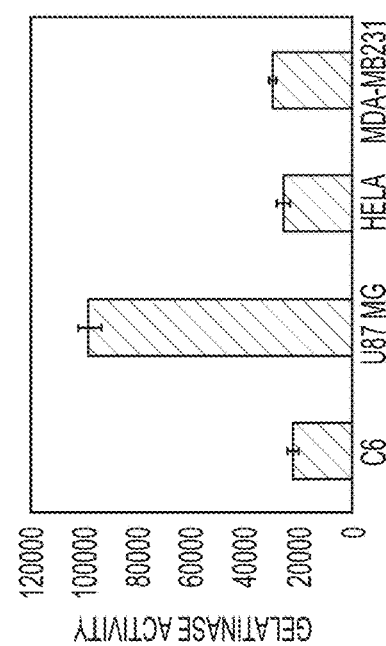
FIG. 12A
FIG. 12B
FIG. 12C

PRECISION CONTROL OF LARGE-SCALE GREEN SYNTHESIS OF BIODEGRADABLE GOLD NANODANDELIONS AS POTENTIAL RADIOTHERANOSTICS

TECHNICAL FIELD OF THE INVENTION

The present invention relates to a type of biodegradable flower-like gold nanoparticle, so-called gold nanodandelion (GND), and a synthesis route thereof. The present invention also demonstrates that GNDs are promising in clinical translation as radiotheranostics

BACKGROUND OF THE INVENTION

Nanomaterials have attracted great interest for several decades because of their excellent unique properties, which allowed their use in a wide range of biomedical applications. In particular, gold nanoparticles (AuNPs) with strong X-ray absorption coefficients have been designed and fabricated as CT contrast agents or radio-sensitizers.

There have been a considerable number of studies over the past two decades interested in the use of AuNPs to augment local radio-therapeutic effects, since Hounsfield and coworkers demonstrated the first AuNP-modulated radiation dose enhancement.

Recently, several research groups showed that smaller AuNPs with larger surface area exhibit more reactive oxygen species (ROS) and stronger X-ray attenuation than larger ones. To date, the obtained experimental reports provided promising evidence for the potential clinical translation of AuNPs with a diameter less than 10 nm. However, several inherent shortcomings need to be overcome for successful clinical application.

First, small AuNPs (i.e. <6 nm) are rapidly eliminated via renal clearance must have insufficient blood circulation time and poor tumor accumulation. Second, compare to AuNPs with a diameter of 50~100 nm, a single AuNPs that is smaller than 50 nm will not produce enough free energy to drive endocytosis. Third, AuNPs of less than 5 nm in size are More likely to induce toxicity than larger ones. In addition, the intracellular aggregation behavior that increases residence time of AuNPs in specific organs, raising concerns of long-term toxicities and immunogenic response.

One strategy to increase the delivery of AuNPs is through the use of polymers or liposomes as nanocarriers, which pack clusters of small AuNPs within cores to exhibit long circulation times and achieve tumor retention. More recently, anisotropic AuNPs (i.e. flowers, urchins, or stars) with high surface density are regarded as another strategy to facilitate the surface-mediated transfer of electrons to drastically enhance ROS generation during radiotherapy.

Although most of the abovementioned strategies exhibit high therapeutic efficacy in vitro and in vivo, clinical translation is not a walk in the park because of a lack of a reliable manner for large-scale synthesis of monodisperse nanoparticles. Next, Ostwald ripening phenomenon that anisotropic AuNPs easily undergo reshaping into spherical particles is largely confined to commercial application.

Moreover, the graduate release of toxic and hazardous by products in physiological environment restricts their use in biomedical applications. Importantly, their long-term accumulation behavior and slow clearance yields in body could result in potential toxicity.

The present invention demonstrates a facile and scalable route to synthesize biodegradable flower-like AuNPs with multi-petals, so-called gold nanodandelions (GNDs). Highly asymmetric "flower-like" GNDs are obtained within a few minutes in the presence of gelatin and ascorbic acid (AA). The methodology adopted here is a simple, feasible, and surfactant-free process, and does not require the usual usage of toxic and hazardous chemicals.

SUMMARY OF THE INVENTION

Accordingly, the present invention relates to a new type of biodegradable flower-like gold nanodandelion (GNU). The branch-shaped geometry of GNDs, which contributes to a greater surface area than the spherical counterpart of similar size does.

A facile and environmentally friendly strategy that uses gelatin as a biodirecting agent is presented for high-yield synthesis of highly monodisperse GNDs. GNDs is obtained through a seed-mediated route, in short, gelatin solution is kept at room temperature with gentle stirring. Then, citrate capped gold seeds and $HAuCl_4$ are added, and this mixture is aged for minutes. The growth of GNDs occurs by adding ascorbic acid aqueous solution. Finally, the GNDs are purified by centrifugation and dispersed in PBS before use.

The present invention provides great advantage over other methods in terms of low cost, green synthesis, and mass production. The morphology, size and number of petals of GNDs can be changed by altering the ratio of [$HAuCl_4$]/[gelatin], seed concentration, and reductant concentration, respectively.

In some embodiments, the ratio of auric acid solution and gelatin solution ([$HAuCl_4$]/[Gelatin](mg mL$^{-1}$)) is between 25 and 50.

In some embodiments, the gold ion concentration of gold seed suspension is between 12.5 and 100 µM.

In some embodiments, the incubation period is between 5 and 30 minutes.

In some embodiments, the concentration of ascorbic acid is between 250 and 1000 µM.

In another aspect, the present invention provides a method for imaging of a subject, which comprising: administering to the subject an effective amount of the gold nanodandelion; and irradiating the subject with a penetrating radiation.

In some embodiments, the penetrating radiation is an X-ray.

In another aspect, the present invention provides a method for enhancing radiosensitivity of a cell population, which comprising: administering to the cell population an effective amount of the gold nanodandelion; and irradiating the cell population with an X-ray.

In some embodiments, the X-ray induces generation of reactive oxygen species (ROS).

In another aspect, the present invention provides a method for treating a cancer in a subject comprising: administering to the subject an effective amount of the gold nanodandelion; and irradiating the subject with an X-ray.

In one embodiment, the cancer is a glioma.

In one embodiment, GNDs undergo self-degradation to smaller sized debris, which is desirable for effective clearance from the body.

Given the above, the present invention demonstrates GNDs are promising in clinical translation as radiotheranostics

BRIEF DESCRIPTION OF THE DRAWINGS

FIGS. 2A-2D depict the characteristics of GNDs: (A) TE micrographs of GNDs; (B) hydrodynamic size; (C) UV-Vis spectra; and (D) XRD pattern of the GNDs; FIGS. 2E-2F depict the HRTEM image of one branch of (E) GNDs and (F) AuNPs.

FIGS. 4I-4L depict the influence of Au seed (concentration of gold ion) (I) 0, (J) 12.5, (K) 25, and (L) 50 µM on the diameter of the as-prepared GNDs. All scale bars are 100 nm.

FIGS. 12A-12C depict the gelatinase activity analysis and in vitro cellular uptake study. (A) Zymography analysis for gelatinase activity was performed from C6 (2), U87 (3), Hela (4), and MDA-MB231 (5); (B) Quantification of gelatinase activities were done with Image J; (C) Visualization of GNDs inside malignant cancer cells.

DETAILED DESCRIPTION OF THE INVENTION

Unless defined otherwise, all technical and scientific terms used herein have the same meaning as commonly understood by a person skilled in the art to which this invention belongs.

As used herein, the term "theranostics" refers to the systematic integration of targeted diagnostics and therapeutics. The theranostics platform includes an imaging component that "sees" the lesions followed by administration of the companion therapy agent that "treats" the same lesions.

As used herein, the term "radio-theranostics" refers to the therapy using ionizing radiation in the theranostic domain.

As used herein, the term "reactive oxygen species (ROS)" refers to the chemically reactive chemical species containing oxygen. Examples include peroxides, superoxide, hydroxyl radical, and singlet oxygen. ROS can damage lipid, DNA, RNA, and proteins, thus induce cell apoptosis.

As used herein, the term "biodegradable" refers to the environmentally friendly products that are biocompatibility, identified degradation mechanism and set of metabolic pathways.

The general protocol used to synthesize the GNDs is based on the reduction of $HAuCl_4$ by AA and gelatin that act as a reductant and stabilizing agent, respectively.

Figure 1:
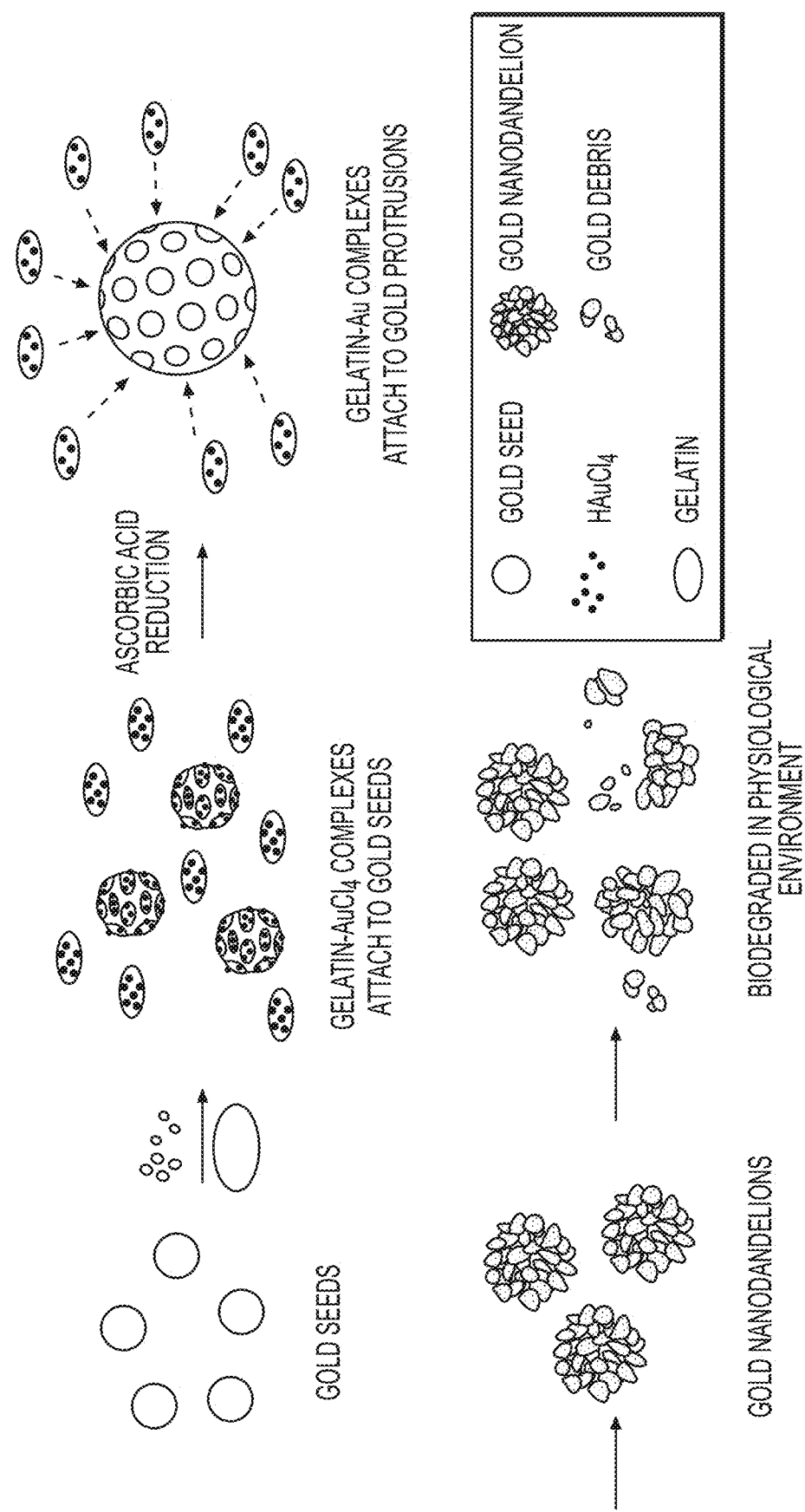
FIG. 1 depicts the schematic diagram of synthesis and degradation of gold nanodandelion.

As illustrated in FIG. 1, Au seeds are stabilized in the gelatin matrix to avoid aggregation during the growth process. Meanwhile, $AuCl_4^-$ ions are trapped by the gelatin to form a relatively stable gelatin-Cl—Au—$Cl_2^-$ complex, which has a lower reduction potential and can postpone the growth of new gold.

Upon reduction of $AuCl_4^-$ by AA, primary $Au^0$ are obtained from complex. Subsequently, AuNP seeds act as the centers to capture free gelatin-Au-complex, leading to the formation of anisotropic multi-branched structures.

With the increase of reaction times, free gelatin-Au-complex diffuses continually toward the hierarchy and deposits further on the empty surface, finally forms thicker petals and roughened surfaces.

The transmission electron microscopy (TEM) images and dynamic light scattering (DLS) measurement reveal that the flower-like morphology of GNDs exhibits a uniform size. The yield of the GNDs is approximately 100% of the particles have numerous petals, where no other shapes are found in any of the analyzed samples.

Hydrogen tetrachloroaurate (III) trihydrate ($HAuCl_4$), trisodium citrate ($Na_3C_6H_5O_7$), L-ascorbic acid ($C_6H_8O_6$), type A gelatin, dihydroethidium (DHE), coumarin-3-carboxylic acid (3-CCA) and 1,3-Diphenylisobenzofuran (DPBF) are purchased from Sigma-Aldrich. All chemicals are used as received without further purification.

α-phospho-H2AX (Millipore, USA) (Dilution—1:1000) and dye conjugated goat anti-mouse Cy 5.5 (GeneTex, USA) are used as secondary antibody. MES-SA (human uterine sarcoma) and U87-MG (human glioblastoma) cell lines are purchased from American Tissue Culture Collection (ATCC). MES-SA and U87-MG cells are cultured using completed McCoy's 5A (Gibco) and DMEM (Gibco), respectively, with the addition of 10% and 1% penicillin-streptomycin antibiotic as per standard. This cell line is incubated at 37° C. in a fully humidified atmosphere of 5% $CO_2$.

Example 1: Synthesis of Gold Seed

Au seed nanoparticles are prepared as following: 3 mL of 38.8 mM of sodium citrate is added to 50 mL of a 1 mM $HAuCl_4$ solution, and the mixture is heated by microwave; After 90 s, the mixture acquires a red-purple color, and then the solution is stored at 4° C.; A transmission electron microscopy (TEM) examination shows that the resulting AuNPs are spherical in shape with an average diameter of 20 nm.

Example 2: Synthesis of Gold Nanodandelions

GNDs are obtained through a seed-mediated route. In short, 4 mL of gelatin solution (10 mg·mL$^{-1}$) is kept at room temperature with gentle stirring. Then, 200 µL of citrate capped gold seeds and 8 µL of 250 mM $HAuCl_4$ are added, and this mixture is aged for 10 min. The growth of GNDs occurs by adding 100 µL of 10 mM ascorbic acid aqueous solution, and stirring is immediately stopped. At the end of the reaction, the solution acquires a purple-blue color. Finally, the GNDs are purified by centrifugation and dispersed in PBS before use (so called gelatin-PEG). For PEG-GNDs synthesis, 10 µL, of 50 mM HS-PEG$_{2000}$ is added to the GNDs and kept stirring for 2 h, Finally, the PEG-GNDs are purified by centrifugation and dispersed in PBS before use.

A representative transmission electron microscopy (TEM) image in FIG. 2A shows that the flower-like morphology of GNDs exhibits a uniform size. The yield of the GNDs is estimated by analyzing hundreds of particles, and approximately 100% of the particles have numerous petals, where no other shapes are found in any of the analyzed samples. The dynamic light scattering (DLS) measurement reveals that the hydrodynamic size of the GNDs is 73±10 nm with high monodispersity (PDI~0.19) and narrow distribution (FIG. 2B). FIG. 2C shows typical characteristics of GNDs, e.g. a single peak at approximately 560 nm, which is in agreement with previous studies. An elemental composition analysis of GNDs using TEM-EDX showed no other elements or impurities in the spectrum, which confirms the GNDs prepared in this study are pure (FIG. 2D). The interplane distance of GNDs is 0.127 nm measured from high resolution TEM (HR-TEM), corresponding to (002) lattice planes, whereas in AuNPs, an interplanar spacing of 0.139 nm is found, corresponding to (111) lattice planes (FIGS. 2E and 2F). This indicates that gelatin plays an essential role in controlling the flower-like shape and orientation of the nanoparticles.

Example 3: The Influence of the Incubation Time

Figure 3A:
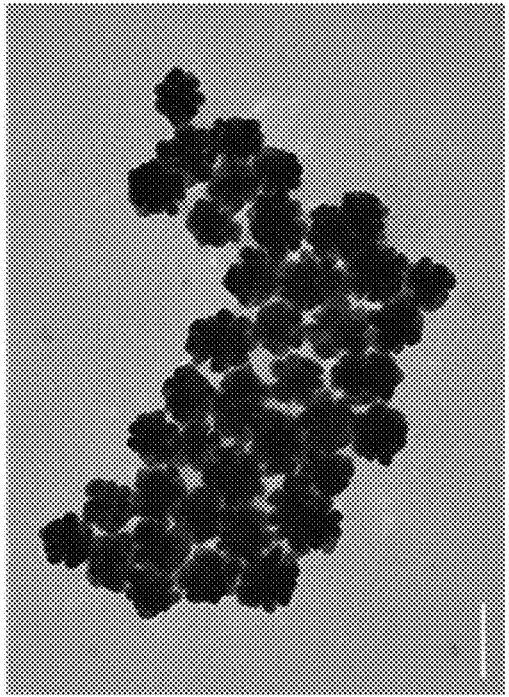
FIGS. 3A-3D depict the influence of gelatin and $HAuCl_4$ co-incubating time of the as-prepared GNDs. The co-incubating time is altered from (A) 0 min, (B) 10 min, (C) 30 min, (D) 60 min. TEM imaging showing the irregular gold nanostructure (arrows) exists after co-incubating gelatin with $HAuCl_4$ for 60 min. Scale bars are 100 nm.

The abovementioned diagram shows that electrostatic attraction between gelatin and $AuCl_4^-$ ions influence the formation of the gelatin-Cl—Au—$Cl_2^-$ complex. In addition, the interaction between gold seed and the amine group of gelatin control the fabrication of nanostructure. To prove this supposition, a series of control experiments, in which the ratio of [$HAuCl_4$]/[gelatin] is fixed, and mediated the incubation time. The irregular gold nanostructure is observed as reductant is added immediately into the reaction solution (FIG. 3A). The result clearly reveals that the initial rate of nuclei formation is faster than gelatin interacts with Au seeds that result in irregular AuNPs.

Figure 3B:
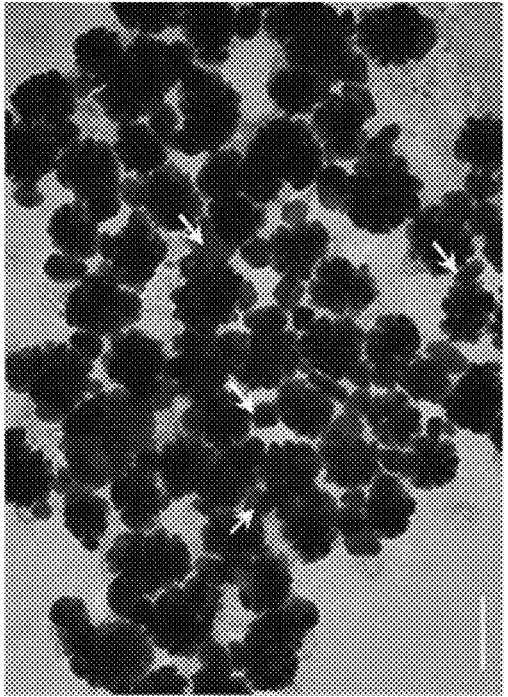
Figure 3C:
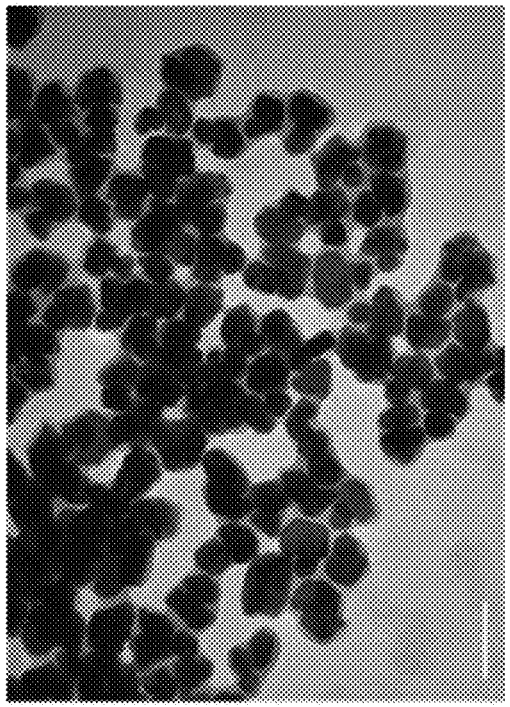
Figure 3D:
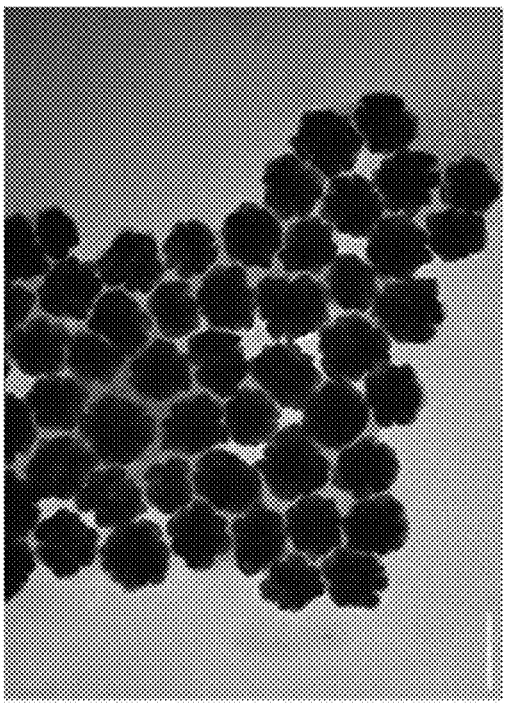

Furthermore, when the incubation time is between 10 and 30 min, the multi-petals GNDs are developed (FIGS. 3B and 3C). This is due to the formation of more gelatin-Cl—Au—$Cl_2^-$ complex and gelatin-capped AuNPs, which guide the subsequent growth of anisotropic structures. Otherwise, it believes that gelatin displays a weak reducing ability, therefore, after extending the incubation time for more than 1 h, a few of irregular nanoparticles has formed along with GNDs (FIG. 3D).

Example 4: The Influence of the Concentration of $HAuCl_4$

Figure 4D:
FIGS. 4A-4D depict the TEM images showing the [$HAuCl_4$]/[Gelatin] ratio: (A) 12.5:1, (B) 25:1, (C) 50:1, and (D) 100:1 affect the morphology of the GNDs.
Figure 4H:
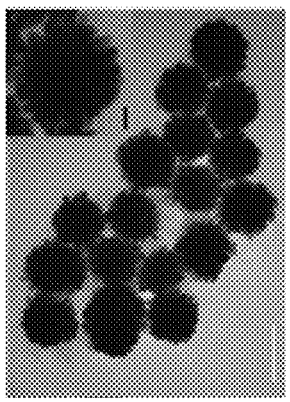
FIGS. 4E-4H depict the influence of (E) 125, (F) 250, (G) 500, and (H) 1000 µM of AA on the petal numbers of the as-prepared GNDs.
Figure 4C:
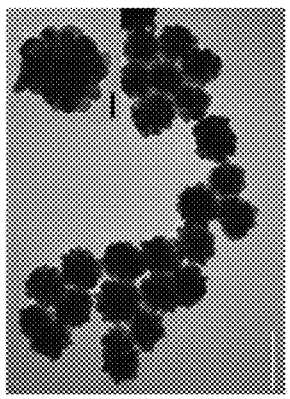
Figure 4G:
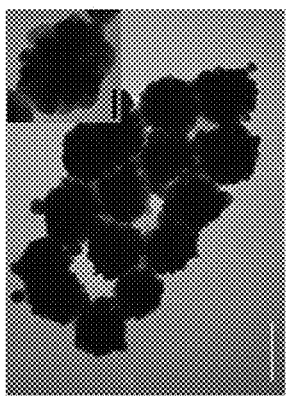
Figure 4B:
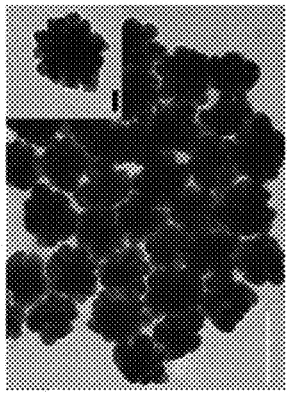

As mentioned above, the attraction between $AuCl_4^-$ ions and gelatin could control the growth and preferential directionality of petals. Hence, the influence of [$HAuCl_4$ (µM)]/[gelatin (mg ml$^-$)] is explored by mediating the concentration of $HAuCl_4$ while keeping the gelatin concentration fixed. The ratio of $HAuCl_4$ to gelatin plays an important role in the formation of uniform flower-like GNDs. Only spherical AuNPs are obtained in the lowest ratio, 12.5 (FIG. 4A). As the proportion of gold ions increased, a direct effect on GNDs with varying morphology is observed. FIGS. 4B and 4C reveal that at the higher ratios of $GNDs_{25:1}$ and $GNDs_{50:1}$ the nanoparticles start to show enlargement of branches. However, when the ratio increases to more than 100, the formation of GNDs with multi-petals is not observed any more. As shown in FIG. 4D, the morphology of $GNTs_{100.1}$ is truncated triangular nanoplates along with some spherical AuNPs.

Example 5: The Influence of the Ratio of [$HAuCl_4$]/[Gelatin]

Figure 5C:
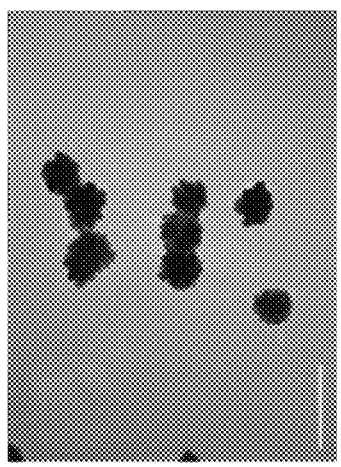
FIGS. 5A-5D depict the TEM for GNDs with various $HAuCl_4$ and gelatin concentration but the [$HAuCl_4$ (µM)]/[Gelatin (mg·mL$^{-1}$)] are fixed: ((A) $GND_{S500:00}$; (B) $GNDs_{250:5}$; (C) $GNDs_{50.1}$. Scale bars are 100 nm; (D) High-yield GNDs in sub-gram scale are routinely prepared.
Figure 5B:
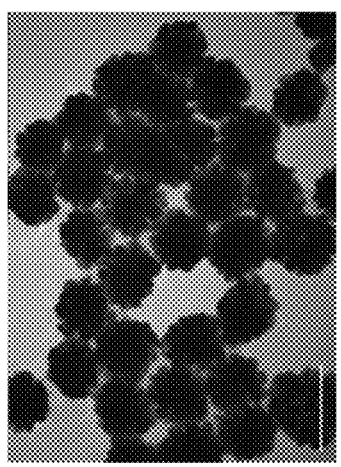
Figure 5A:
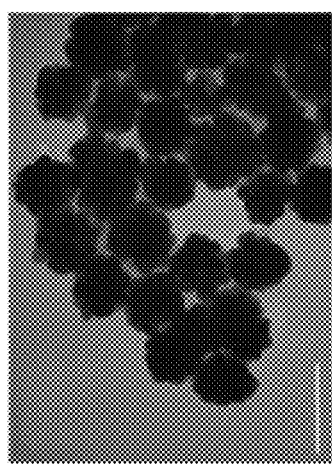
Figure 5D:
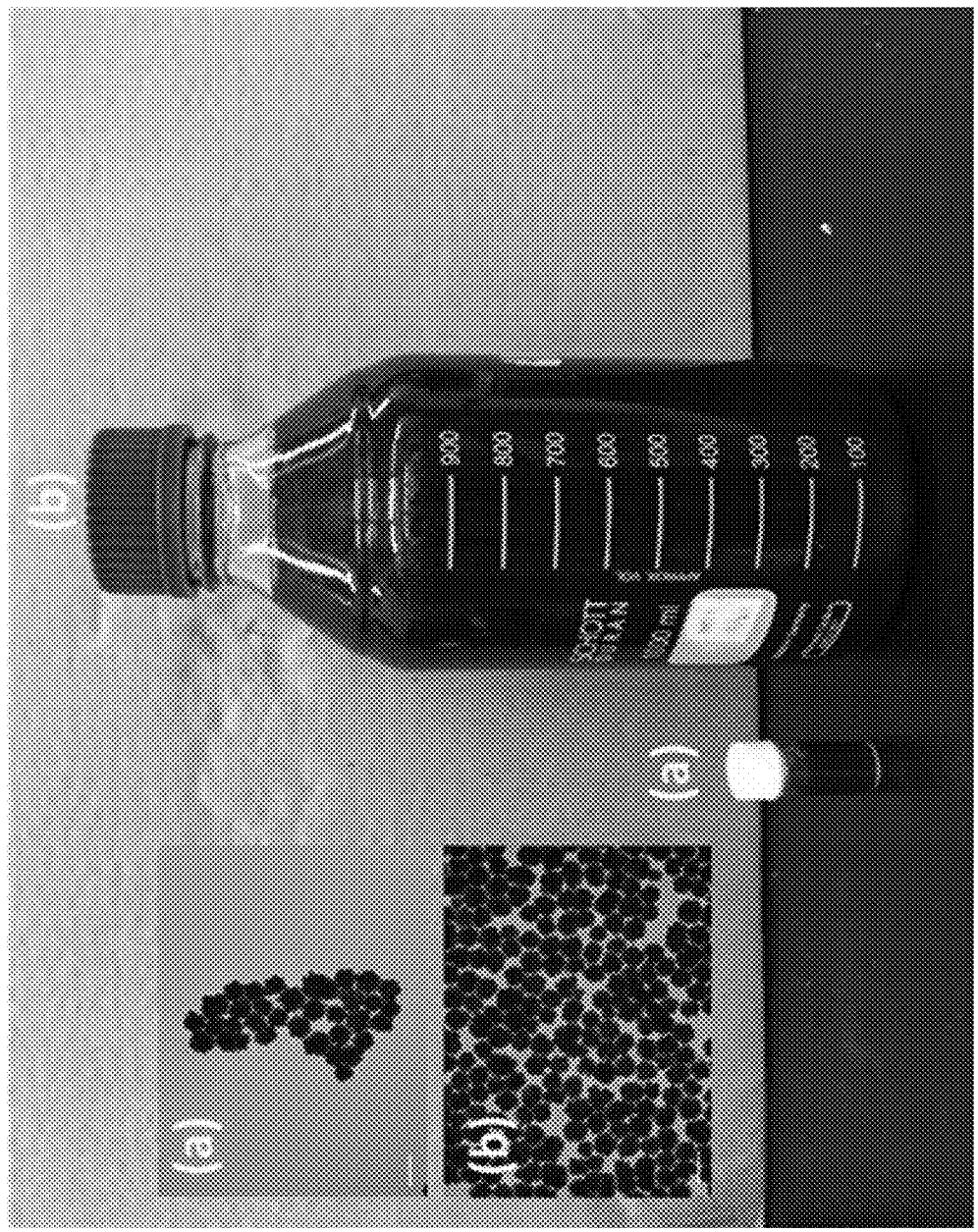

To prove the ratio of [$HAuCl_4$]/[gelatin] is the determining factor for varied morphology but not the concentration of gelatin or $HAuCl_4$, as a control experiment, GNDs with varying concentrations of $HAuCl_4$ and gelatin with their ratios fixed are synthesized $GNDs_{500:10}$, $GNDs_{250:5}$, and $GNDs_{50:1}$. From the TEM observations, the size of $GNDs_{50:1}$ is slightly smaller than $GNDs_{250:5}$ and $GNDs_{500:10}$ and the synthesized NPs are mainly multi-petals (see FIG. 5A-C). Rapid reduction of $Au^{3+}$ to $Au^0$ is necessary to promote the anisotropic growth of Au branches, however, it also limits the scalable synthesis of gold nanostructures with high yield and homogeneity. The characteristic of our established GNDs benefits scale up synthesis under a minimum reaction volume. As showed in FIG. 5D, while keeping the identical growth parameters (the concentrations of 500 µM $HAuCl_4$, 10 mg·mL$^{-1}$, and 250 µM AA in 1 L reaction volume), a sub-gram scale quantity of nearly monodisperse GNDs are readily synthesized.

Example 6: The Influence of the Concentration of Ascorbic Acid and Gold Seed

Figure 4F:
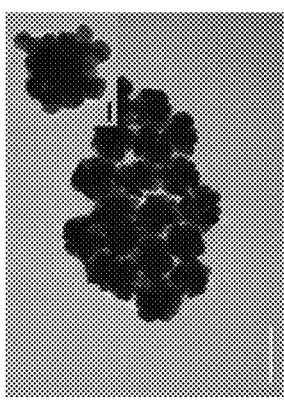
Figure 4A:
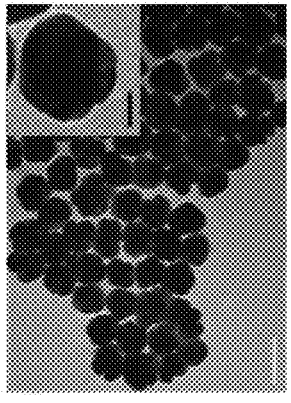
Figure 4E:
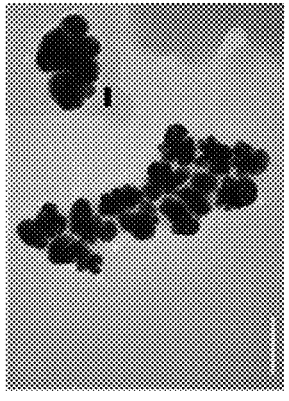

Represented in FIG. 4E-F are the examples of TEM images of GNDs in the presence of varying amounts of reductant while maintaining all other conditions constant. At very low concentrations (125 µM AA), nanoparticles of average size ~40 nm having irregular structures are obtained. Furthermore, we have found that that GND petals are increasing steadily when AA concentration≥250 µM.

The influence of the seed concentration (concentration of gold ion) on the properties of the as-prepared GNDs is studied in this section. As the amount of seeds increases from 0 to 50 μM, the as-prepared NPs retain a multi-branched structure, but a clear decrease in the diameters is observed (FIG. 4I-L). As the amount of seed reached 100 μM, GNDs with a smaller size and fewer branches are observed. Obviously, the addition of fewer seeds led to a higher $Au^0$/seed ratio, providing more $Au^0$ to supply the growth of each GNDs. As a result, the formation of bigger GNDs is favoured.

Example 6: The Internalization and Degradation of Gold Nanodandelions

It is commonly believed that internalized nanoparticles deliver a highly inhomogeneous distribution of energy on the sub-cellular scale upon X-ray irradiation, thus leading to a larger extent of DNA damage, meaning that cellular distribution of nanoparticles will have a direct influence on the degree of radio-sensitization. For this reason, the internalization of GNDs is first investigated. To measure the amount of gold nanomaterials expelled by cells, three-dimensional tumor spheroids are used in this study, Brief, U87-MG cells are seeded into 2% agarose precoated 24-well plates at a density of $1\times10^4$ cells/well. Five days later, the spheroids are exposed to 4 μg mL$^{-1}$ either GNDs or AuNPs. After 24 h incubation, spheroids are rinsed with ice-cold PBS twice and the medium was replaced with fresh medium without gold nanomaterials. To eliminate the extracellular gold nanomaterials, the medium is removed every day and the spheroids were collected at 0, 3, 10, and 17 day. The experiments are conducted in triplicate. The mass of gold determined from the ICP-MS is reported in ppb of gold per sample.

Their cell uptake is observed after 24 h incubation with either GNDs or spherical AuNPs in the cell culture medium. As show in FIG. 6, most of nanostructures presented in the perinuclear region. Due to the most of low energy electrons deposit within tens of nanometers of the vicinity of a nanostructure during radiation therapy, particle localization in close proximity to the nucleus is particularly important in DNA damage.

Figure 6A:
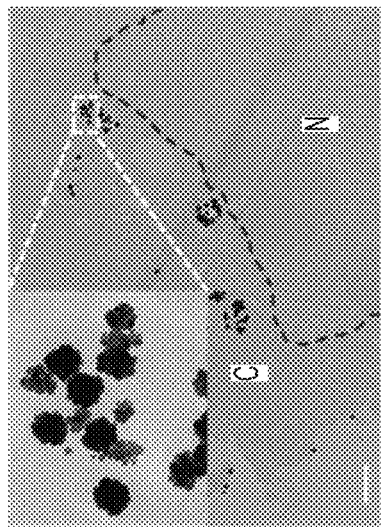
FIGS. 6A-6F depict the representative TEM images of intracellular uptake of (A) GNDs and (B) AuNPs in MES-SA cells. N: nucleus. C: cytoplasm; (C) Representative EDX spectrum from pretreated GNDs at 10 mM GSH concentration. Inset: TEM images of GNDs after treating with 10 mM GSH for 2 days. TEM images showed the dissociated state of GNDs (arrows) at the (D) 1st day, and (E) 3rd day in MES-SA cells; (F) The amount of internalized gold in U87-MG 3D spheroid measured by ICP-MS at each passage.
Figure 6B:
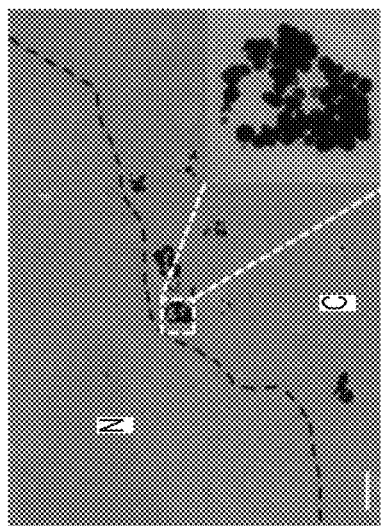
Figure 6C:
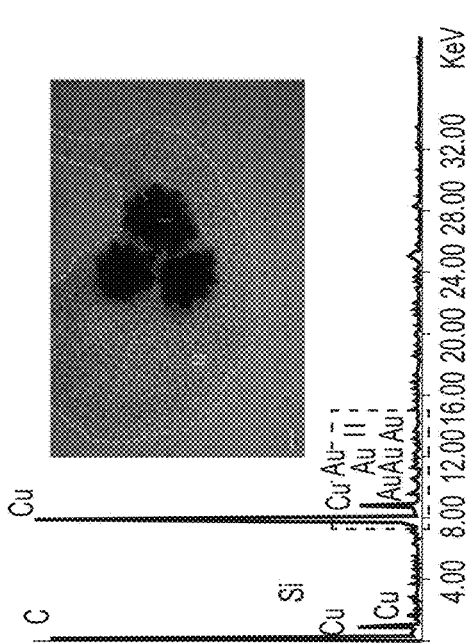
Figure 6D:
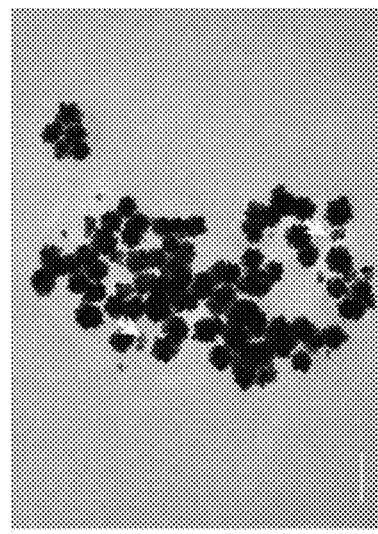
Figure 6E:
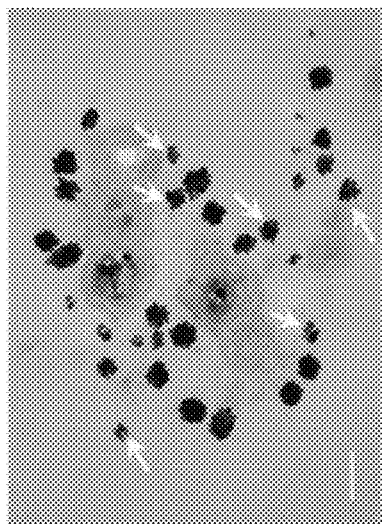
Figure 6F:
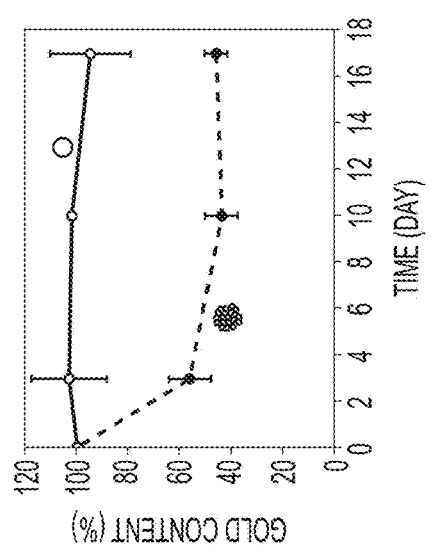

One interesting observation from the TEM images depicts that GNDs appear monodispersed and some gold debris are found (FIG. 6A). The biodegradability of the GNDs is further investigated by subjecting them to different incubation times. As revealed from FIG. 6D, one day after cell uptake, a minority of these GNDs gradually collapse. The collapse of GNDs in cell on the 3rd days is further confirmed by TEM analysis (FIG. 6E). It is worth noting that the percentage of collapsed GNDs further increases with incubation time. This indicates that GNDs undergo metabolic degradation under physiological condition. In comparison, spherical AuNPs that cluster as larger aggregation are observed inside cells (FIG. 6B). The biodegradation of GNDs is further confirmed by treating with PBS buffer with 2 mM of glutathione to mimic the physiological environment. After 48 h of incubation, the diameter of GNDs shrinks from 65 nm to approximately 50 nm, and accompanies by ultra-small nanoparticles (FIG. 6C). To investigate the composition of ultra-small nanoparticles, we have performed an EDX analysis at the site of spots. An EDX spectrum is also shown in FIG. 6C and confirms the major element is Au. Furthermore, another in vitro experiment is conducted to understand the degradation dynamics of GNDs. To exclude gold content dilution behavior from cell proliferation, 3D 1187-MG spheroid model is employed and continuously observed for up to 17 days and examined with ICP-MS analysis. It is striking to see that gold content in GNDs-incubated spheroid decreases to approximately 45% with the elongated time, indicating GNDs are successively expelled out (FIG. 6F).

Figure 7A:
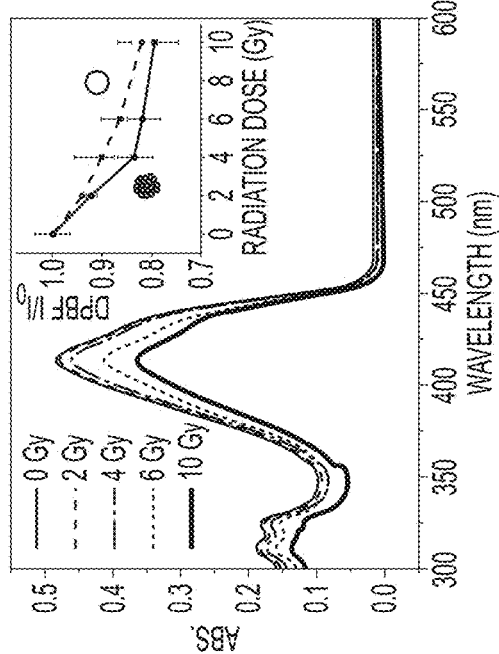
FIG. 7A depicts the CT scan images and HU values of GNDs and spherical AuNPs.

Example 7: The Potential of GNDs as a CT Contrast Agent and Radio-Sensitizer in Comparison to Spherical AuNPs As seen in the inset of FIG. 7A, visibly brighter contrast is observed for GNDs at concentrations higher than 0.6 mg mL$^{-1}$ in comparison to spherical ones. This has also been measured quantitatively in Hounsfield units, which revealed that GNDs showed greater X-ray attenuation than spherical ones, by the extent of ~18% in the attenuation intensity (indicated by $[HU_{GNDs}-HU_{AuNPs}]/[HU_{AuNPs}]$). This result may be attributed to the branch-shaped geometry of GNDs, which contributes to a greater surface area than the spherical counterpart of similar size.

In addition to CT contrast enhancements, the radio-sensitization properties are investigated by examining the ROS production. For the quantification of ROS, three specific species, ·OH, $O_2^{·-}$, and singlet oxygen ($^1O_2$), are chosen for their biological importance. The generation of these species is measured by three kinds of probes, DPBF (absorbance: 414 nm), DHE (emission: 585 nm), and 3-CCA (emission: 450 nm) dedicate to the quantification of integrated amounts of $^1O_2$, $O_2^{·-}$ and ·OH, respectively. GNDs are suspended with 500 μL PBS for ROS measurement. A ROS probe is premixed with GNDs and then diluted by PBS for the designed final concentration. The resulting final concentrations of DPBF, DHE and 3-CCA are 30, 25, and 50 μM, respectively. Solutions are then exposed to X-rays using a commercial cabinet X-ray system with the standard X-ray tube operated at 160 kV and 25 mA. Singlet oxygen measurements are made by following the loss of fluorescence intensity of DBPF in the aqueous GNDs solutions. In DHE measurements, the solution is excited at 465 nm and its fluorescence intensity is measured for super oxide generation. In the 3-CCA measurement, hydroxyl radical is measured by following the increase of fluorescence intensity.

Figure 7B:
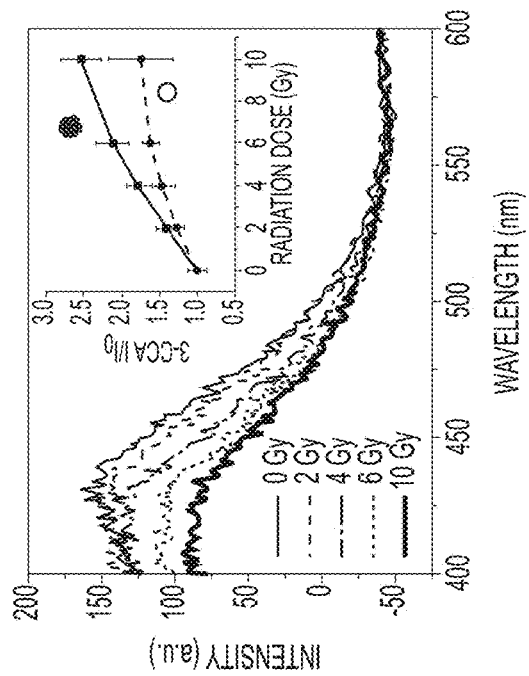
FIGS. 7B-7D depict the generation of (B) $^1O_2$; C) $O_2^{·-}$ and (D) OH with GNDs and AuNPs under the X-ray irradiation.

For the singlet oxygen detection, FIG. 7B illustrates the photobleaching of DPBF in PBS with gold nanomaterials compares to the pristine DPBF control (nanoparticle-free) group. The steep decrease of DPBF absorption in either GND or spherical AuNP suspensions reflects the efficient generation of highly reactive $^1O_2$.

Figure 7C:
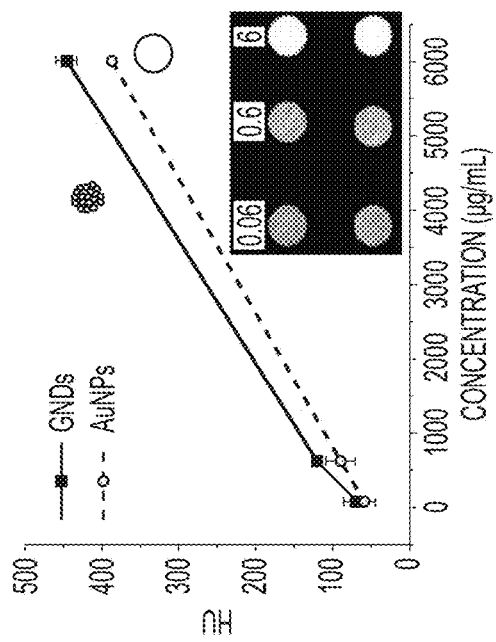
Figure 7D:
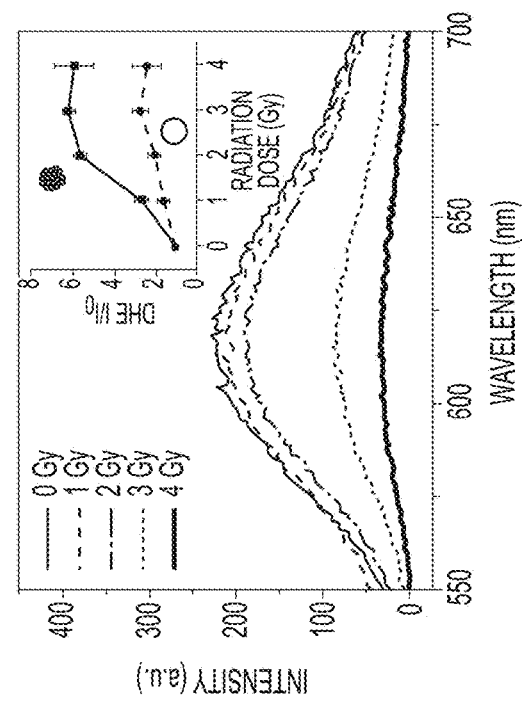

Other biologically important ROS, such as ·OH and $O_2^{·-}$, FIGS. 7C and 7D illustrate the obvious change in the fluorescence intensity of DHE and 3-CCA as a function of X-ray irradiation dose. The quantitation of $O_2^{·-}$ and ·OH generation appeared in the insets of FIGS. 7C and 7D, which plot the ratio of the intensities ($I/I_0$) at 585 nm of DHE and at 450 nm of 3-CCA, respectively. From these data, one can clearly observe the enhanced generation from the presence of gold nanomaterials, especially GNDs upon X-ray irradiation.

The intensities in FIG. 7B-D show significant variations, the results suggest that both nanostructures enhance ROS production. Furthermore, the radio-sensitization effect of GNDs is found superior spherical ones, especially in $O_2^{·-}$ production. The results suggest that GNDs to enhance the generation of ROS might correlate to the satellite effect of petals and high surface areas to decrease internal absorption.

Example 8: Concentration-Dependent In Vitro Toxicity of GNOs

Figure 8B:
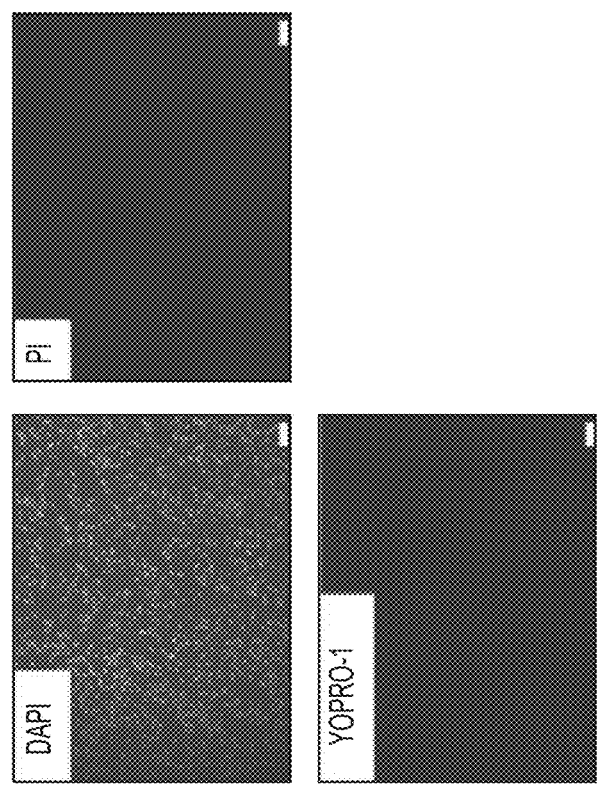
FIG. 8B depicts fluorescent microscopy images showing the early and late apoptosis of C6 after treating with gelatin-GNDs. YOPRO-1 (green) and propidium iodide signals (red) denote leakage of the cell and nuclear membranes, respectively.
Figure 8A:
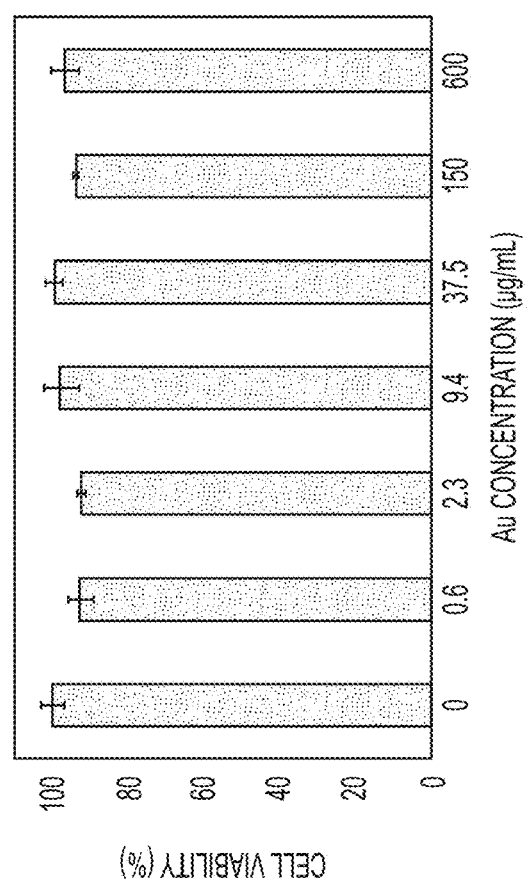
FIG. 8A depicts concentration-dependent in vitro toxicity of GNDs after 24 h. The results show that the GNDs has no significant toxicity.
Figure 9B:
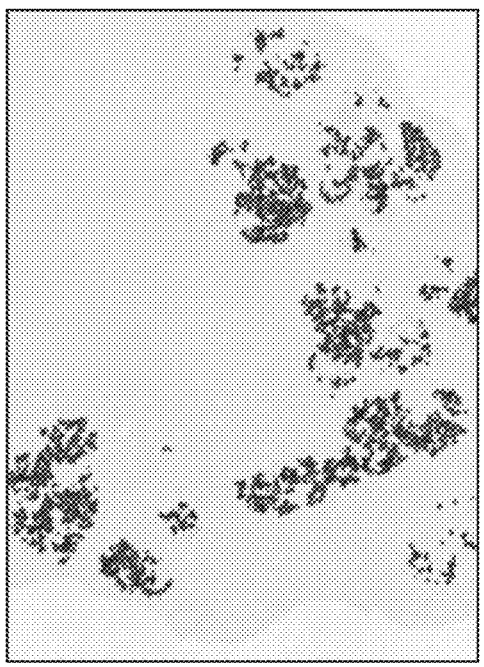
FIGS. 9A-9D depict the representative CT contrast (bottom) and phantom images of MMP-responsive GNDs (top).
Figure 9D:
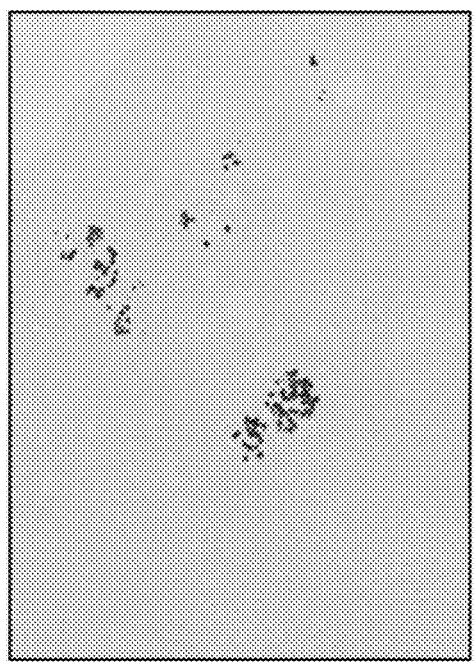
Figure 9A:
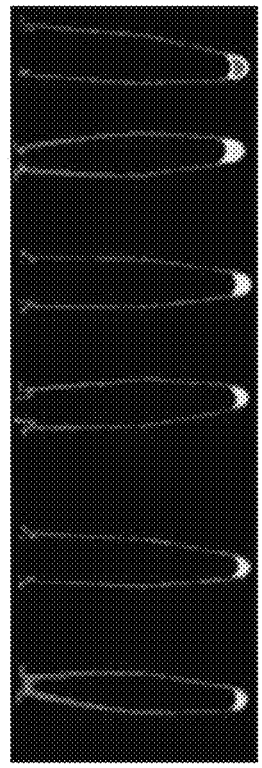
Figure 9C:
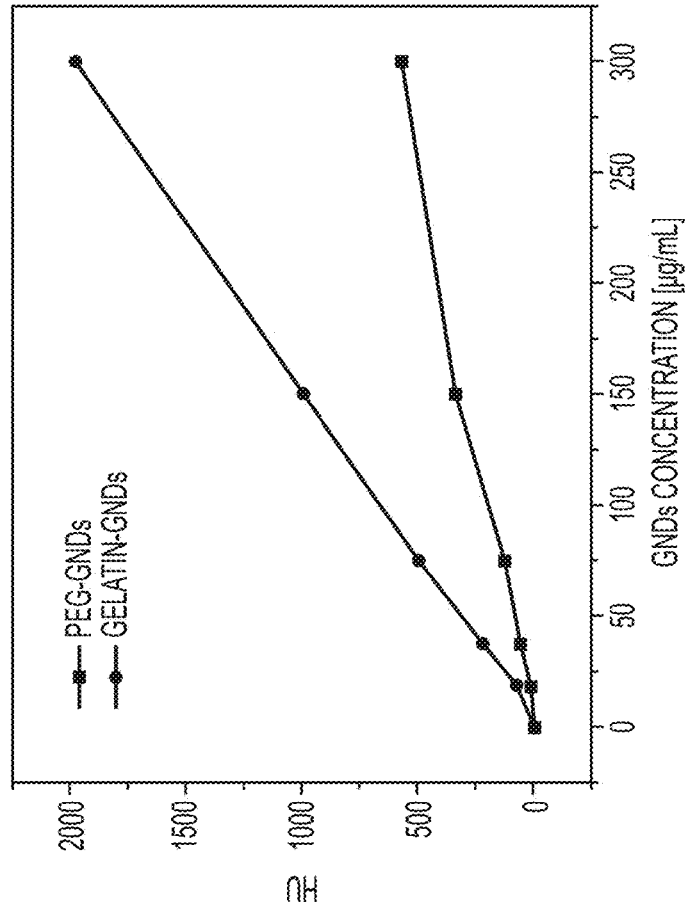

For biomedical applications, it is essential to evaluate the cytotoxicity of our established GNDs. To determine the cytotoxicity, cell viability is determined by MTT assay and YOPRO-1/PI staining kit. It is clearly evident from FIG. 8 that MES-SA cells treated with different concentrations ranging from 0.6 to 600 µg·mL$^{-1}$ of PEG-GNDs exhibited no significant cell viability after incubation for 24 h. Consistent with the MIT assay, the cell viability of C6 (rat glioma cell) is examined by YOPRO-1/PI staining, which also exhibits negligible cytotoxicity toward C6 cells.

Example 9: Cell CT-Imaging of MMP-Responsive GNDs

To further study CT-imaging ability of MMP-responsive GNDs, U87 MG cells are allowed to co-incubate with either gelatin-GNDs or PEG-GNDs. FIG. 9 shows the CT images of gelatin-GNDs treated cells in the range of 18.75-300 µg·mL$^{-1}$. Brighter CT images are observed with increasing gelatin-GNDs concentration. Compare with PEG-GNDs, substantially increased (3 to 4 folds) CT signal intensity is detectable in gelatin-GNDs treated cells.

Example 10: Irreversible DNA Damage Induced by the Synergistic Effects of GNDs and X-Ray Radiation To further evaluate the radio-sensitization effect of GNDs in vitro, radio-resistant glioma cell, U87-MG, is irradiated (5 Gy) and observed double-stranded DNA damage via γ-H2AX staining to confirm the synergistic DNA damage induced by the synergistic effects of GNDs and X-ray radiation, Phosphorylated histone H2AX is widely regarded as a molecular marker for DNA double-stranded break. Briefly, after different treatment for 24 h, cells are washed twice with PBS, fixed with 4% glutaraldehyde for 10 min, and permeabilized with 0.5% Triton X-100. Next, cells are blocked in 5% bovine serum albumin for 1 h, and subsequently incubated overnight at 4° C. with monoclonal anti-human phospho-H2AX (S139) mouse mAb (Millipore, USA) at 1:1000 dilution in PBS (with 0.1% Triton X-100 and 5% BSA). Cells are washed with PBS and then incubated with goat anti-mouse Cy5.5 secondary antibody (GeneTex) at 1:1000 dilution in PBS (with 0.1% Triton X-100 and 5% BSA) for 1 h at room temperature. Nuclei are stained blue with Hoechst 33342.

Figure 10A:
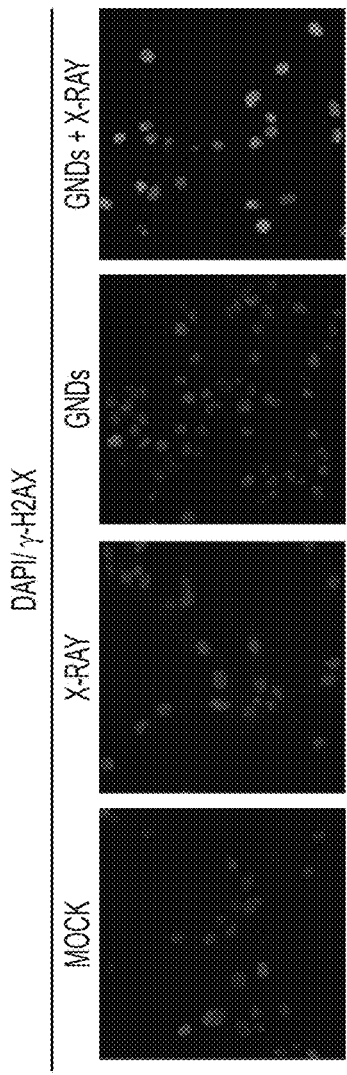
FIGS. 10A-10B depict the radiation exposure of radio-resistant glioma U87-MG cells. (A) Representative images of γ-H2AX foci and (B) their quantification of cells has a specific foci class for cells counted per condition after exposure to 5 Gy radiation.
Figure 10B:
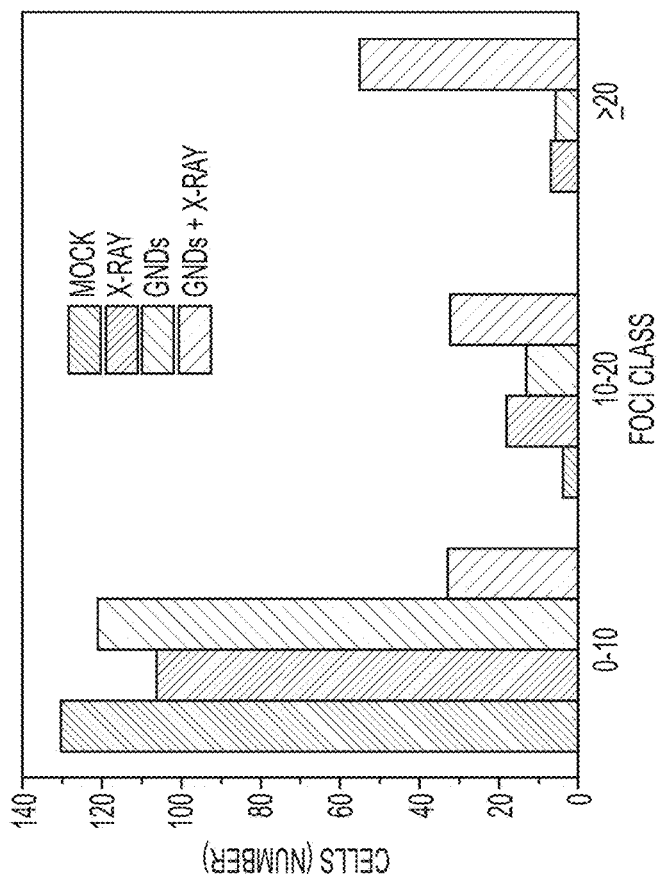

As shown in FIG. 10A, minimal or no γ-H2AX foci are observed in the untreated control and cells treated with GNDs. The only X-ray treated cells reveal a slightly higher number of γ-H2AX foci in comparison. However, it is observed that the cells receive the combination treatment displayed highly significant number of γ-H2AX foci formations (FIG. 10B). This result verifies that the intracellular enhancement of induced irreversible DNA damage.

Figure 11:
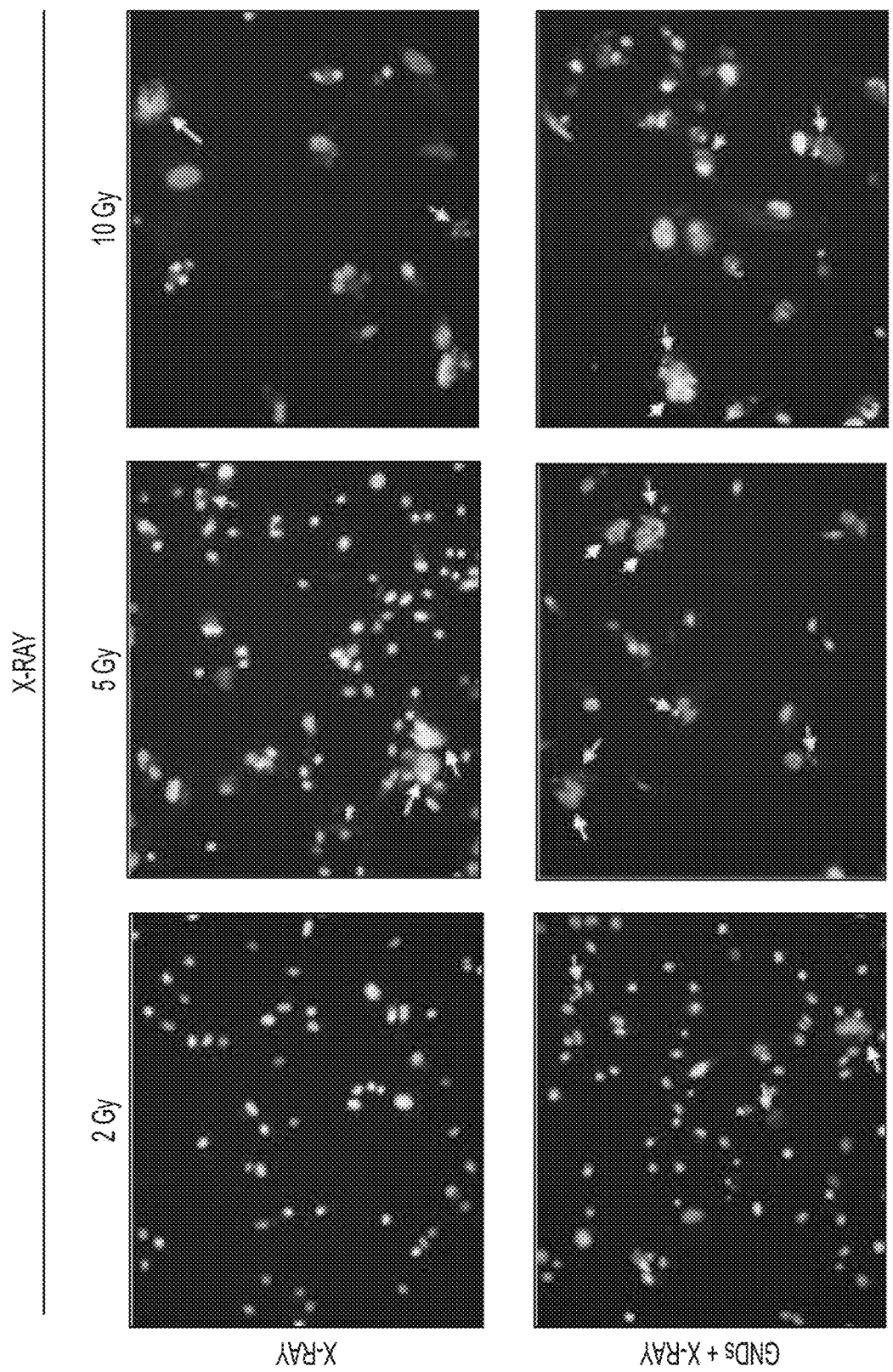
FIG. 11 depicts the abnormal nuclei in irradiated U87-MG cell. DAPI staining of irradiated cells displaying mitotic aberrations. The accumulative GNDs enhance the ROS generation and increase frequencies of micronuclei (yellow), multi-lobulated nuclei (white).

Example 11: The Dysfunctional Mitosis Induced by the Synergistic Effects of GNDs and X-Ray Radiation To further confirm these results, we also analyse changes in nucleus morphology following X-ray irradiation. As shown in FIG. 11, the formation of multi-lobulated nuclei or cells with several micronuclei, a sign of mitotic catastrophe, are observed in a dose-dependent way 4 days after X-ray irradiation. The dysfunctional mitosis is consistent with the observed a significant double-stranded DNA damage (FIG. 10), implying the accumulative and irreversible DNA damage induces a delayed type of apoptosis.

Example 12: Enhanced GND Intracellular Accumulation of MMP Overexpressed Cancer Cells In order to enhance the therapeutic outcome and minimize side effects to the normal tissues, nanocarriers that respond to tumor microenvironment stimuli such as pH, redox potential, and enzymes are of particular interest. Several studies about tumor development and metastasis found that matrix metalloproteases (MMPs) are ubiquitously overexpressed and actively involved in tumor development. Therefore, MMPs are widely used as an attractive tumor specific stimuli in targeted drug delivery. In this study, gelatin, a substrate of MMP-2/MMP-9 is used as a biodirecting agent to synthesize GNDs. Therefore, our established GNDs (so-called gelatin-GNDs) is MMP-responsive for enhance intracellular accumulation. To confirm the enhanced intracellular accumulation, MMP-2 and -9 overexpressed cancer cells such as C6, U87 MG, Hela and MDA-MB 231 are selected for zymography assay (FIG. 12). Since these cells are confirmed for MMP-2/9 overexpression, we further apply them for in vitro experiment. After 24 hr of incubation with 150 µg·mL$^{-1}$ of gelatin-CiNDs containing 10% FBS, a large number of GNDs are Observed in most of cells, especially U87 MG and Hela.

Figures 13A, 13B:
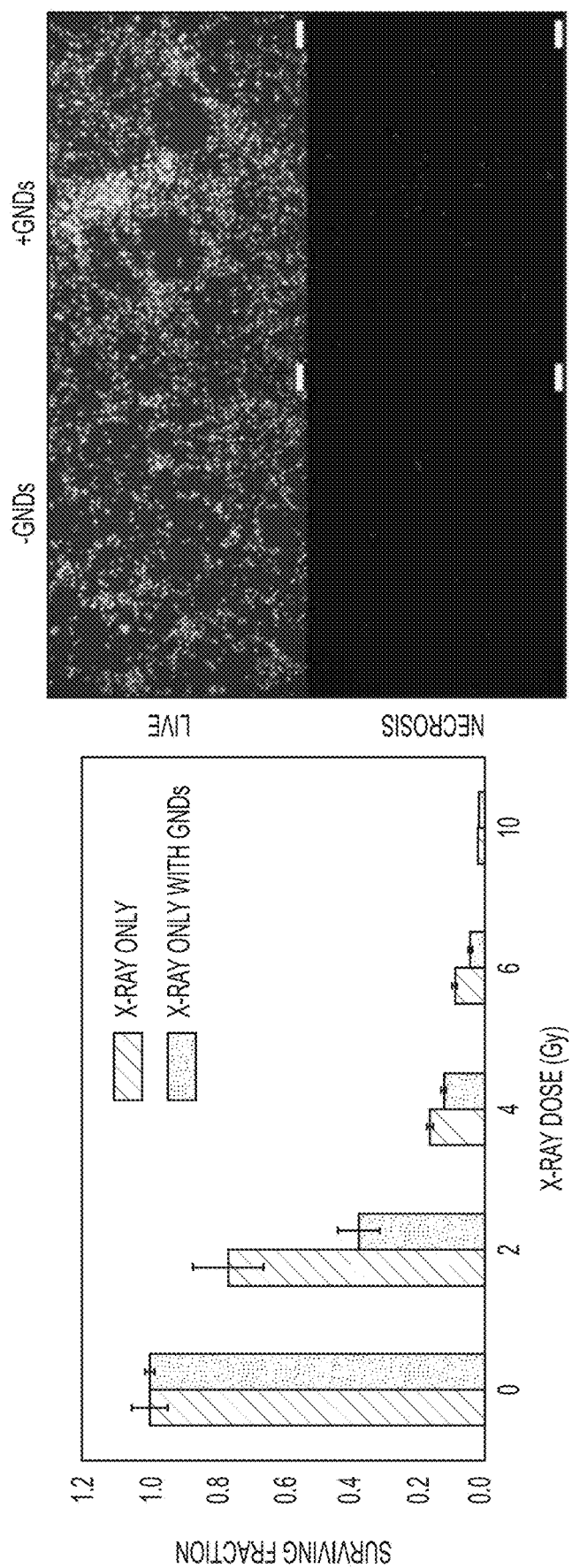
FIGS. 13A-13B depict the GNDs radiosensitized C6 glioma cells. (A) C6 cells was treated with gelatin coated GNDs (with 10% FBS for 18 h) radiosensitization by clonogenic cell survival immediately after irradiation. (B) fluorescence microscopy images showed that accumulated GNDs enhanced the efficiency of radiotherapy and pushed cells to death mechanisms.
Figure 14A:
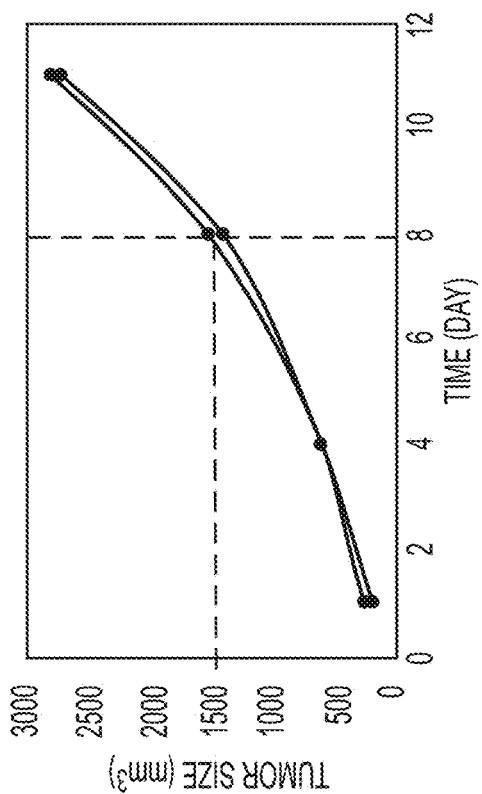
FIGS. 14A-14D depict GNDs increase the efficacy of sub-optimal radiation therapy. (A) mock; (B) GNDs only; (C) X-ray, no GNDs; (D) X-ray plus GNDs.
Figure 14B:
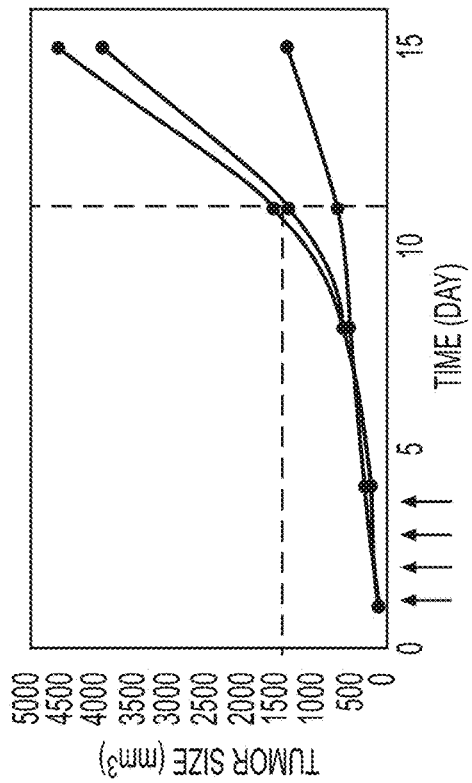
Figure 14C:
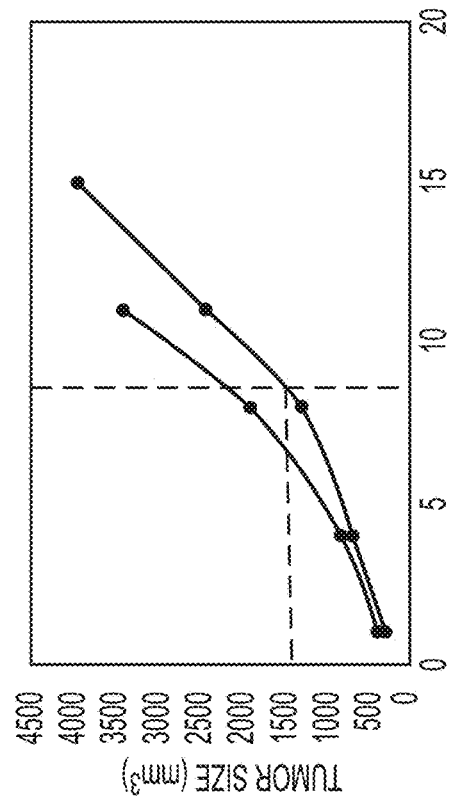
Figure 14D:
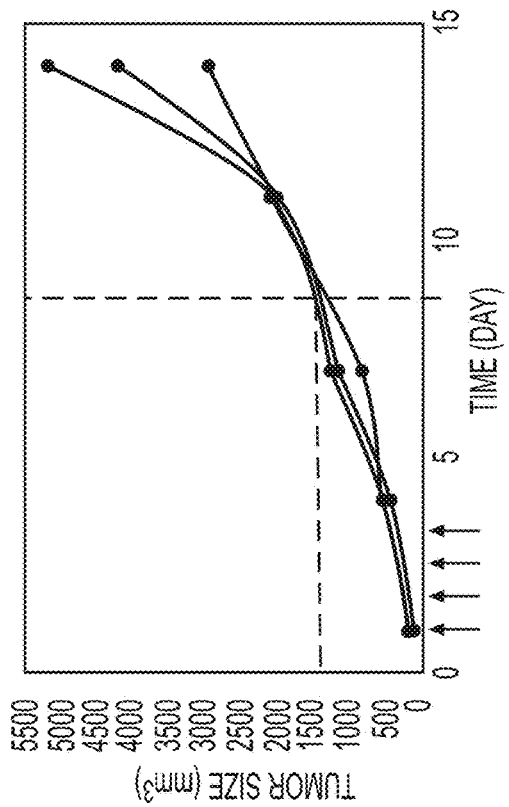

Example 13: Radiosensitizing Effects of Gelatin-GNDs in C6 Tumor Bearing Nude Mice To determine the efficacy of gelatin-GNDs on radiosensitization using, clonogenic cell survival assay is performed. As shown in FIG. 13, after irradiation in the presence of gelatin-GNDs, C6 cell colony reveals a significantly decreased survival compared to the groups that receive irradiation alone. To further examine the radiosensitizing effects of gelatin-GNDs in vivo, C6 tumor bearing nude mice is established as the animal model. As shown in FIG. 14, as compared with the control and other treatment groups, mice treated with gelatin-GNDs and radiation demonstrated tumor growth delay inhibiting effect from day 4 to 7 respectively.

In summary, a facile and environmentally friendly strategy that uses gelatin as a biodirecting agent is presented for high-yield synthesis of highly monodisperse GNDs. The present invention provides great advantage over other methods in terms of low cost, green synthesis, and mass production. The morphology, size and number of petals of GNDs can be changed by altering the ratio of [HAuCl$_4$]/[gelatin], seed concentration, and reductant concentration, respectively. Some embodiments that involved ROS production reveals that the CT contrast enhancing GNDs also pronounce more ROS generation than conventional AuNPs that enables its application as second-generation radiosensitizer for potential clinical theranostics. Subsequently, GNDs undergo self-degradation to smaller sized debris, which is desirable for effective clearance from the body. Overall, all of these benefits promise a new efficient theranostic modality for in vivo animal and clinical uses.

The invention claimed is:
1. A method for fabricating a gold nanoparticle, comprising the steps of:
adding a gold seed suspension and an auric acid solution to a gelatin solution to form a mixture;
incubating the mixture for an incubation period; and
adding a reductant to the mixture,
wherein the incubation period is between 5 and 30 minutes.

2. The method according to claim 1, wherein the gelatin solution comprises type A gelatin.

3. The method according to claim 1, wherein a ratio of auric acid solution and the gelatin solution ([auric acid] (μM)/[Gelatin](mg mL$^{-1}$)) is between 25 and 50.

4. The method according to claim 1, wherein the auric acid is chloroauric acid (HAuCl$_4$).

5. The method according to claim 1, wherein a gold ion concentration of the gold seed suspension is between 12.5 and 100 μM.

6. The method according to claim 1, wherein the reductant is ascorbic acid.

7. The method according to claim 6, wherein a concentration of ascorbic acid is between 250 and 1000 μM.

8. A method for imaging of a subject, which comprises:
administering to the subject an effective amount of the gold nanoparticle fabricated according to claim 1; and
irradiating the subject with a penetrating radiation.

9. The method according to claim 8, wherein the penetrating radiation is an X-ray.

10. A method for enhancing radiosensitivity of a cell population, which comprises:
administering to the cell population an effective amount of the gold nanoparticle fabricated according to claim 1; and
irradiating the cell population with an X-ray.

11. The method according to claim 10, wherein the X-ray induces generation of reactive oxygen species (ROS).

12. A method for treating a cancer in a subject comprising:
administering to the subject an effective amount of the gold nanoparticle fabricated according to claim 1; and
irradiating the subject with an X-ray.

13. The method according to claim 12, wherein the cancer is a glioma.

* * * * *